United States Patent [19]

Ienaga et al.

[11] Patent Number: 4,708,961
[45] Date of Patent: Nov. 24, 1987

[54] ACYLINDOLE DERIVATIVES AND THEIR USE IN PHARMACEUTICAL COMPOSITIONS

[76] Inventors: Kazuharu Ienaga; Ko Nakamura, both of c/o Institute of Bio-Active Science, Nippon Zoki Pharmaceutical Co., Ltd. 442-1, Aza Kawakitayama, Kinashi, Yashiro-cho, Katoh-gun, Hyogo, Japan

[21] Appl. No.: 919,746

[22] Filed: Oct. 16, 1986

Related U.S. Application Data

[63] Continuation of Ser. No. 655,472, Sep. 27, 1984, abandoned.

[30] Foreign Application Priority Data

Sep. 28, 1983 [JP] Japan ................................ 58-181084
Aug. 11, 1984 [JP] Japan ................................ 59-168928

[51] Int. Cl.$^4$ .................... C07D 209/12; A61K 31/40
[52] U.S. Cl. ..................................... 514/423; 548/493
[58] Field of Search ........................ 548/493; 514/423

[56] References Cited

FOREIGN PATENT DOCUMENTS 6009761 1/1982 Japan ................................. 548/493

OTHER PUBLICATIONS

Chemical Abstracts, vol. 82, No. 21, p. 85, No. 133482y, May 26, 1975.
Chemical Abstracts, vol. 83, No. 7, p. 421, No. 58569X, Aug. 18, 1975.
Tetrahedron Letters, vol. 22, No. 47, pp. 4751–4754, 1981.
Journal of the Chemical Society, Part I, pp. 625–628 (1957).
Powell et al, Chemical Abstracts, vol. 96, No. 142006n, 1982.

Primary Examiner—Robert T. Bond
Assistant Examiner—W. B. Springer
Attorney, Agent, or Firm—Pennie & Edmonds

[57] ABSTRACT

The present invention is concerned with novel acylindole derivatives of the formula (I) and platelet-aggregation inhibiting agents containing them as an active ingredient.

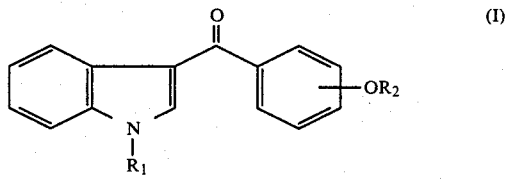

In the formula (I), either $R_1$ and $R_2$ is hydrogen, an alkyl group having 1 to 5 carbon atoms, an alkyl group substituted by at least one hydroxy group and having 1 to 5 carbon atoms, or a group of the formula

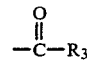

in which $R_3$ is an alkyl group having 1 to 5 carbon atoms, and $-OR_2$ is a substituent at the ortho or para position.

The compounds of the invention are useful as preventive medicine or remedy for various diseases or symptoms caused by platelet-aggregation, as well as inhibitors of platelet-aggregation on vascular walls during or after an operation.

15 Claims, No Drawings

ACYLINDOLE DERIVATIVES AND THEIR USE IN PHARMACEUTICAL COMPOSITIONS

This is a continuation of application Ser. No. 655,472 filed Sept. 27, 1984, abandoned.

TECHNICAL FIELD

The present invention relates to novel acylindole derivatives and their pharmaceutically acceptable salts as well as to pharmaceutical compositions which contain at least one of these compounds as an active ingredient.

BACKGROUND

Various types of thrombosis, in particular, cerebral thrombosis, cerebral infarction caused by obstruction, and ischemic heart disease, are serious medical and social problems. Therefore, scientists and doctors have conducted extensive research and development for cures, remedies, or methods for preventing these problems.

DESCRIPTION OF THE INVENTION

The present invention relates to acylindole derivatives which prevent or remedy thrombosis and have an excellent inhibitory effect on platelet-aggregation as well as low toxicity, and have utility for treating or preventing thrombosis type disorders.

The present invention relates to new acylindole derivatives and pharmaceutically acceptable salts thereof, to a process for preparing such new acylindole derivatives and pharmaceutically acceptable salts, and to pharmaceutical compositions containing at least one of these new acylindole derivatives or pharmaceutically acceptable salts as an active ingredient.

The acylindole derivative of the present invention is represented by the formula (I):

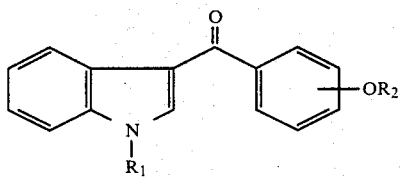

wherein either $R_1$ or $R_2$ is hydrogen, an alkyl group having 1 to 5 carbon atoms, an alkyl group having 1 to 5 carbon atoms containing one or more hydroxy groups, or a group of the formula

in which $R_3$ is an alkyl group having 1 to 5 carbon atoms. Also, $R_1$ and $R_2$ may be the same or a different substituent and $-OR_2$ can be substituted at the ortho or para position. The alkyl groups may be straight or branched chain.

Advantageously, $R_1$ and/or $R_2$ is hydrogen; a methyl, ethyl, n-propyl, iso-propyl, n-butyl, iso-butyl, sec-butyl, t-butyl or pentyl group; a hydroxymethyl, hydroxyethyl, dihydroxyethyl, hydroxypropyl, dihydroxypropyl, trihydroxypropyl, hydroxybutyl, dihydroxybutyl, trihydroxybutyl or tetrahydroxybutyl group; an acetyl, propionyl, butanoyl, pentanoyl or hexanoyl group.

Especially advantageous compounds of the present invention include the following:
3-(p-methoxybenzoyl)indole,
3-(o-methoxybenzoyl)indole,
3-(p-hydroxybenzoyl)indole,
3-(o-hydroxybenzoyl)indole,
3-(p-methoxybenzoyl)-N-acetylindole,
3-(o-methoxybenzoyl)-N-acetylindole,
3-(p-acetoxybenzoyl)-N-acetylindole,
3-(p-methoxybenzoyl)-N-methylindole,
3-(p-isopropoxybenzoyl)indole,
3-(p-isopropoxybenzoyl)-N-isopropylindole,
3-(p-hydroxybenzoyl)-N-ethylindole,
3-(p-ethoxybenzoyl)indole,
3-(p-ethoxybenzoyl)-N-ethylindole,
3-(p-hydroxybenzoyl)-N-(hydroxymethyl)indole,
3-[p-(2-hydroxyethoxy)benzoyl]indole,
3-[p-(2,3-dihydroxypropoxy)benzoyl]indole,
3-(p-hydroxybenzoyl)-N-(2,3-dihydroxypropyl)indole,
3-[p-(2,3-dihydroxypropoxy)benzoyl]-N-(2,3-dihydroxypropyl)indole,
3-(o-hydroxybenzoyl)-N-(2,3-dihydroxypropyl)indole,
3-[o-(2,3-dihydroxypropoxy)benzoyl]-N-(2,3-dihydroxypropyl)indole,
3-(p-methoxybenzoyl)-N-(2-hydroxyethyl)indole,
3-(o-methoxybenzoyl)-N-(2,3-dihydroxypropyl)indole,
3-[p-(3-hydroxypropoxy)benzoyl]indole,
3-[p-(3-hydroxypropoxy)benzoyl]-N-(3-hydroxypropyl)indole.

The acylindole compounds according to the present invention are produced by conventional processes, such as for example, by introducing an acyl group into an indole as described hereinbelow:

(1) After reacting the indole compound with a Grignard reagent, an acid chloride having an acyl residue corresponding to the intended acylindole derivative ($R_2COCl$) is reacted therewith in an inert solvent while heating at an appropriate temperature for one to several hours.

(2) The indole and an amide compound having an acyl residue corresponding to the intended acylindole derivative ($R_2CONR'_2$, $R'$ being a $C_{1-4}$ lower alkyl group) are reacted in the presence of phosphorus oxychloride in an appropriate solvent while heating at an appropriate temperature for one to several hours.

Furthermore, the obtained acylindole compounds may be converted to other acylindole derivatives of the invention by well-known methods, such as acylation, alkylation, deacylation and dealkylation. Typical conversion processes are described hereinbelow:

(1) An acylindole derivative is reacted with a halogenated alkane or halogenated hydroxyalkane, which corresponds to the intended derivative (halogenated $R_1H$ or halogenated $R_2H$), in the presence of a base such as sodium alkoxide, sodium hydroxide or potassium hydroxide and an inert solvent at room temperature, or if desired, by heating to a higher temperature. When an alkoxide is employed, the inert solvent can be alcohol or dimethylformamide. On the other hand, when a hydroxide is employed, a solvent such as water, alcohol or mixtures thereof, can be used.

(2) An acylindole derivative is reacted with aldehyde which corresponds to the intended derivative ($R_1CHO$ or $R_2CHO$) in the presence of acid in aqueous solution at room temperature, or if desired, by heating to higher temperatures.

(3) An acylindole is reacted with carboxylic acid or anhydride thereof which has an acyl residue corresponding to the intended derivative ($R_3COOH$ or $R_3OCOOR_3$) in the presence of acid or base catalyst in an appropriate inert solvent at room temperature, or if desired, by heating to higher temperatures.

The present invention also includes pharmaceutically acceptable salts of the compounds of the above-mentioned formula (I). These include salts of alkali metals such as lithium, sodium or potassium, alkaline earth metals such as calcium or magnesium, other metals such as aluminum, or organic bases such as ammonia, trimethylamine, triethylamine or tris(hydroxymethyl)aminomethane. These salts may be produced from free acylindole derivatives or converted with each other in a manner which is well known to those skilled in the art.

EXAMPLES

The scope of the invention is further described in connection with the following examples, which are set forth for purposes of illustration only and are not to be construed as limiting the scope of the invention in any manner. These examples describe the preparation of compounds according to the present invention.

EXAMPLE 1

30 ml of ether solution containing 4.0 g of indole were added to 10 ml of ether solution containing 5.0 g of methylmagnesium iodide. And then 30 ml of ether solution containing 5.7 g of anisoyl chloride were added dropwise to the solution. The reaction mixture was allowed to stand for several hours and further refluxed for 3 hours. After cooling, the reaction mixture was washed with aqueous solution of sodium hydrogencarbonate. The obtained organic layer was evaporated to dryness under reduced pressure. After purification by chromatography on silica gel and recrystallization from ethanol, 3-(p-methoxybenzoyl)indole (compound 1) was obtained in the form of white crystals. (Yield: 42%)

m.p.: 200°–200.5° C.

IR(KBr): 3195, 1608, 1590, 1433 cm$^{-1}$.

GNMR(DMSO-d$_6$): $\delta = 3.90$(s,3H), 7.08(d,2H,J=8 Hz), 7.1–7.4 (m,2H), 7.4–7.6(m,1H), 7.82(d,2H,J=8 Hz), 7.94(s, 1H), 8.1–8.3(m,1H), 13.9(brs,1H).

MS: M$^+$: 251, m/z: 220, 144, 116, 89, 63.

EXAMPLE 2

2.6 g of indole and 8.6 g of N,N-dimethylanisamide were added to 2.6 ml of phosphorus oxychloride. The mixture was heated at 80°–85° C. for 3 hours. After cooling, 50 ml of ether was added to the mixture. The reaction mixture was then poured into water and pH value was adjusted to 10 with aqueous solution of sodium hydroxide. The resulting precipitate was filtered out and then recrystallized from ethanol to obtain compound 1 in the form of white crystals. (Yield: 56%)

In the same way as described in Examples 1 or 2, the following compound was obtained.

3-(o-methoxybenzoyl)indole (compound 2) (Yield: 56%).

m.p.: 210°–211° C.

IR(KBr): 3075, 1595, 1442, 746 cm$^{-1}$.

NMR(DMSO-d$_6$): $\delta = 3.70$(s,3H), 6.9–7.7(m,7H), 7.60(s,

1H), 8.0–8.4(m,1H), 12.0(brs,1H).

MS: M$^+$: 251, m/z: 234, 144, 116, 89, 63.

EXAMPLE 3

1 g of compound 1 and 3 g of pyridine hydrochloride were heated at 215° C. for 1 hour in a nitrogen atmosphere. After the mixture was cool,1.5 N hydrochloric acid was added thereto and then the supernatant was removed by centrifugation. The precipitate was dissolved in methanol which contains 10% of aqueous solution of sodium hydroxide, followed by filtering out the resulting precipitate. The obtained solution was acidified to give a crude product. The crude product was recrystallized from ethyl acetate to give 3-(p-hydroxybenzoyl)indole (compound 3). (Yield: 66%).

m.p.: 288°–288.5° C.

IR(KBr): 3190, 1612, 1596, 1220 cm$^{-1}$.

NMR(DMSO-d$_6$): $\delta = 6.88$(d,2H,J=8 Hz), 7.1–7.3(m,2H), 7.4–7.6(m,1H), 7.70(d,2H,J=8 Hz), 7.94(s,1H), 8.1–8.3(m,1H), 10.1(brs,1H), 13.9(brs,1H).

MS: M$^+$: 237, m/z: 220, 144, 116, 89, 65.

In the same way, the following compound was obtained.

3-(o-hydroxybenzoyl)indole (compound 4) (Yield: 56%).

m.p.: 165°–165.5° C.

IR(KBr): 3260, 1555, 1441, 1200, 700 cm$^{-1}$.

NMR(DMSO-d$_6$): $\delta = 6.8$–7.8(m,7H), 7.97(d,1H,J=3 Hz), 8.0–8.4(m,1H), 10.8(brs,1H), 12.0(brs,1H).

MS: M$^+$: 237, m/z: 144, 117, 89.

EXAMPLE 4

1 g of compound 1 was added to the mixture of 50 ml each of acetic anhydride and pyridine, and then the solution was stirred overnight at room temperature. The reaction mixture was evaporated to dryness under reduced pressure. The resulting crude crystals were recrystallized from chloroform to obtain 3-(p-methoxybenzoyl)-N-acetylindole (compound 5) in the form of white crystals. (Yield: 90%).

m.p.: 159°–160° C.

IR(KBr): 3125, 1720, 1620, 1600, 1212 cm$^{-1}$.

NMR(DMSO-d$_6$): $\delta = 2.66$(s,3H), 3.88(s,3H), 6.98(d,2H,J=8 Hz), 7.2–7.6(m,2H), 7.85(s,1H), 7.86(d,2H,J=8 Hz), 8.0–8.5(m,2H).

MS: M$^+$: 293, m/z: 251, 220, 144, 108, 92, 77, 56.

In the same way, the following compounds were obtained.

3-(o-methoxybenzoyl)-N-acetylindole (compound 6) (Yield: 92%).

m.p.: 133°–134° C.

IR(KBr): 1724, 1640, 1212, 1020, 762 cm$^{-1}$.

NMR(DMSO-d$_6$): $\delta = 2.68$(s,3H), 3.77(s,3H), 6.9–7.7(m,6H), 7.81(s,1H), 8.0–8.5(m,2H).

MS: M$^+$: 293, m/z: 251, 234, 165, 144, 116, 92, 77, 51.

3-(p-acetoxybenzoyl)-N-acetylindole (compound 7) (Yield: 84%).

m.p.: 153°–153.5° C.

IR(KBr): 1749, 1718, 1216 cm$^{-1}$.

NMR(CDCl$_3$): $\delta = 2.30$(s,3H), 2.61(s,3H), 7.19(d,2H,J=8 Hz), 7.1–7.6(m,2H), 7.80(s,1H), 7.85(d,2H,J=8 Hz), 8.0–8.5(m,2H).

MS: M$^+$: 321, m/z: 279, 237, 208, 144, 116, 89.

EXAMPLE 5

1 g of compound 1 was dissolved in 30 ml of dimethylformamide and the solution was stirred at room temperature. 258 mg of sodium methoxide was added to the solution, followed by stirring for 30 minutes. Then,678 mg of methyl iodide was added dropwise to the solution and the reaction was continued for 1 hour. The reaction mixture was evaporated to dryness under reduced pressure, followed by addition of ethyl acetate and washing with water. The organic layer was dried over anhydrous sodium sulfate and the solvent was removed. The obtained crude product was recrystallized from ethanol to give 3-(p-methoxybenzoyl)-N-methylindole (compound 8) in the form of white platy crystals. (Yield: 94%).

m.p.: 143.5°–144° C.
IR(KBr): 1612, 1594, 1248, 741 cm$^{-1}$.
NMR(DMSO-d$_6$): $\delta = 3.85(s,3H)$, $3.87(s,3H)$, $7.06(d,2H,J=8$ Hz), $7.0-7.8(m,3H)$, $7.80(d,2H,J=8$ Hz), $7.98(s,1H)$, $8.1-8.4(m,1H)$.
MS: M$^+$: 265, m/z: 222, 158, 102.

In the same way, the following compounds were obtained.

3-(p-isopropoxybenzoyl)indole (compound 9) (Yield: 51%).

m.p.: 202°–203° C.
IR(KBr): 3146, 2970, 1592, 1427, 745 cm$^{-1}$.
NMR(DMSO-d$_6$): $\delta = 1.30(d,6H,J=6$ Hz), $4.4-5.0(m,1H)$, $7.01(d,2H,J=8$ Hz), $7.0-7.8(m,3H)$, $7.79(d,2H,J=8$ Hz), $7.95(brs,1H)$, $8.1-8.4(m,1H)$, $11.65(brs,1H)$.
MS: M$^+$: 279, m/z: 237, 208, 144, 116, 89.

3-(p-isopropoxybenzoyl)-N-isopropylindole (compound 10) (Yield: 34%)

m.p.: (oily substance).
IR(CHCl$_3$): 2980, 1600, 1382, 1250, 883 cm$^{-1}$.
NMR(CDCl$_3$): $\delta = 1.38(d,6H,J=6$ Hz), $1.55(d,6H,J=6$ Hz), $4.4-5.0(m,2H)$, $6.91(d,2H,J=8$ Hz), $7.0-7.5(m,3H)$, $7.65(s,1H)$, $7.77(d,2H,J=8$ Hz), $8.1-8.5(m,1H)$.
MS: M$^+$: 321, m/z: 306, 279, 264, 237, 208, 186, 144, 121, 89, 65.

3-(p-hydroxybenzoyl)-N-ethylindole (compound 11).
m.p.: 211°–212° C.
IR(KBr): 3250, 1572, 1382, 1210 cm$^{-1}$.
NMR(DMSO-d$_6$): $\delta = 1.43(t,3H,J=6$ Hz), $4.34(q,2H,J=6$ Hz),
$6.9-7.7(m,3H)$, $6.98(d,2H,J=8$ Hz), $7.82(d,2H,J=8$ Hz), $8.07(s,1H)$, $8.1-8.4(m,1H)$, $10.2(brs,1H)$.
MS: M$^+$: 265, m/z: 250, 236, 208, 172, 144, 116.

3-(p-ethoxybenzoyl)indole (compound 12).
m.p.: 193°–194° C.
IR(KBr): 3150, 2955, 1586, 1597, 1440, 1240, 720 cm$^{-1}$.
NMR(CDCl$_3$): $\delta = 1.36(t,3H,J=6$ Hz), $4.11(q,2H,J=6$ Hz), $6.9-7.7(m,3H)$, $7.03(d,2H,J=8$ Hz), $7.7-8.0(m,1H)$, $7.81(d,2H,J=8$ Hz), $8.0-8.4(m,1H)$, $12.05(brs,1H)$.
MS: M$^+$: 265, m/z: 236, 208, 144, 116, 89.

3-(p-ethoxybenzoyl)-N-ethylindole (compound 13).
m.p.: 118°–119° C.
IR(KBr): 2980, 1613, 1596, 1380, 1242, 740 cm$^{-1}$.
NMR(DMSO-d$_6$): $\delta = 1.32(t,3H,J=6$ Hz), $1.36(t,3H,J=6$ Hz), $4.07(q,2H,J=6$ Hz), $4.27(q,2H,J=6$ Hz), $6.9-7.7(m,3H)$, $7.02(d,2H,J=8$ Hz), $7.83(d,2H,J=8$ Hz), $8.02(s,1H)$, $8.0-8.4(m,1H)$.
MS: M$^+$: 293, m/z: 279, 265, 237, 209, 172, 144, 116.

EXAMPLE 6

500 mg of 3-(p-hydroxybenzoyl)indole was dissolved in 37% of aqueous solution of formaldehyde and 2 ml of acetic acid. The solution was refluxed for 1 hour in oil bath. After cooling, the solution was evaporated to dryness. The residue was purified by thin layer chromatography on silica gel, and recrystallized from ethyl acetate to give 3-(p-hydroxybenzol)N-(hydroxymethyl)indole (compound 14) in the form of white needle crystals. (Yield: 44.4%).

m.p.: 188°–190° C.
IR(KBr): 3050, 2740, 1600, 1382, 1018 cm$^{-1}$.
NMR(DMSO-d$_6$): $\delta = 5.62(s,2H)$, $6.68(brs,1H)$, $6.92(d,2H,J=8.7$ Hz), $7.2-7.4(m,2H)$, $7.68(dd,1H,J_1=1.5$ Hz,$J_2=6.8$ Hz), $7.74(d,2H,J=8.7$ Hz), $8.05(s,1H)$, $8.23(dd,1H,J_1=1.5$ Hz,$J_2=6.8$ Hz), $10.15(brs,1H)$.
MS: M$^+$: 237, m/z: 220, 144, 116, 89.

EXAMPLE 7

7 g of 3-(p-hydroxybenzoyl)indole and 1.44 g of sodium hydroxide were dissolved in 200 ml of a mixture of ethanol and water (ethanol:water=1:1). 2.85 g of 2-chloroethanol was added to the solution followed by reflux for 3 hours in oil bath. The solvent was evaporated to dryness and the residue was extracted with water-ethyl acetate. The organic layer obtained was purified by column chromatography on silica gel to give a crude product. It was recrystallized from ethyl acetate to obtain 3-[p-(2-hydroxyethoxy)benzoyl]indole (compound 15) in the form of white needle crystals. (Yield: 54%).

m.p.: 196°–197° C.
IR(KBr): 3250, 2925, 1600, 1590, 1422 cm$^{-1}$.
NMR(DMSO-d$_6$): $\delta = 3.76(dt,2H,J_1=4.8$ Hz,$J_2=4.8$ Hz), $4.09(t,2H,J=4.8$ Hz), $4.93(t,1H,J=4.8$ Hz), $7.07(d,2H,J=8.7$ Hz), $7.2-7.3(m,2H)$, $7.51(dd,1H,J_1=1.5$ Hz,$J_2=6.8$ Hz), $7.79(d,2H,J=8.7$ Hz), $7.94(s,1H)$, $8.21(dd,1H,J_1=1.5$ Hz,$J_2=6.8$ Hz), $12.00(brs,1H)$.
MS: M$^+$: 281, m/z: 264, 236, 144, 116.

EXAMPLE 8

11 g of 3-(p-hydroxybenzoyl)indole and 7.43 g of sodium hydroxide were dissolved in 10 ml of water. 20.51 g of 3-chloro-1,2-propandiol was added to the solution followed by reflux with stirring for 3 hours in oil bath. After cooling, the solution was evaporated to dryness. The residue was purified by column chromatography on silica gel. After recrystallization from ethyl acetate, 3-[p-(2,3-dihydroxypropoxy)benzoyl]indole (compound 16) was obtained in the form of white crystals. (Yield: 13.8%).

m.p.: 178°–180° C.,
IR(KBr): 3350, 3160, 1600, 1438, 1244 cm$^{-1}$.
NMR(DMSO-d$_6$): $\delta = 3.47(dd,2H,J_1=5.5$ Hz,$J_2=5.5$ Hz), $3.83(m,1H)$, $3.95(dd,1H,J_1=6.2$ Hz,$J_2=10.3$ Hz), $4.10(dd,1H,J_1=4.4$ Hz,$J_2=10.3$ Hz), $4.72(t,1H,J=5.5$ Hz), $5.02(d,1H,J=5.2$ Hz), $7.07(d,2H,J=8.7$ Hz), $7.1-7.3(m,2H)$, $7.51(dd,1H,J_1=1.5$ Hz,$J_2=6.8$ Hz), $7.79(d,2H,J=8.7$ Hz), $7.94(s,1H)$, $8.21(dd,1H,J_1=1.5$ Hz,$J_2=6.8$ Hz), $12.01(brs,1H)$.
MS: M$^+$: 311, m/z: 237, 181, 144.

In the same way, the following compounds were obtained.

3-(p-hydroxybenzoyl)-N-(2,3-dihydroxypropyl)indole (compound 17) (Yield: 15.9%).

m.p.: 175°–177° C.,
IR(KBr): 3250, 2930, 1602, 1581, 1378 cm$^{-1}$.
NMR(DMSO-d$_6$): $\delta = 3.32(dd,1H,J_1=4.5$ Hz,$J_2=10.3$ Hz), $3.40(dd,1H,J_1=4.5$ Hz,$J_2=10.3$ Hz), $3.7-3.9(m,1H)$, $4.14(dd,1H,J_1=6.2$ Hz,$J_2=10.3$ Hz), $4.41(dd,1H,J_1=4.4$ Hz,$J_2=10.3$ Hz), $4.85(t,1H,J=4.5$ Hz), $5.08(d,1H,J=5.2$ Hz), $6.89(d,2H,J=8.7$ Hz), 7.2–7.4(m,2H), 7.59(dd,1H,$J_1$=1.5 Hz,$J_2$=6.8 Hz), 7.72(d,2H,J=8.7 Hz), 7.93(s,1H), 8.23(dd,1H,$J_1$=1.5 Hz,$J_2$=6.8 Hz), 10.11(brs,1H).

MS: M+: 311, m/z: 280, 250, 237, 144, 121.

3-[p-(2,3-dihydroxypropoxy)benzoyl]-N-(2,3-dihydroxypropyl)indole (compound 18) (Yield: 33.7%).

m.p.: 155°–157° C.,

IR(KBr): 3340, 2910, 2850, 1600, 1580, 1384 cm$^{-1}$.

NMR(DMSO-$d_6$): δ=3.32(dd,1H,$J_1$=5.4 Hz,$J_2$=10.5 Hz), 3.40(dd,1H,$J_1$=5.4 Hz,$J_2$=10.5 Hz), 3.47(t,2H,J=5.4 Hz), 3.7–3.9(m,2H), 3.97(dd,1H,$J_1$=6.1 Hz,$J_2$=10.0 Hz), 4.11(dd,1H,$J_1$=4.2 Hz,$J_2$=10.0 Hz), 4.14(dd,1H,$J_1$=7.8 Hz,$J_2$=14.2 Hz), 4.42(dd,1H,$J_1$=3.4 Hz,$J_2$=14.2 Hz), 4.72(t,1H,J=5.4 Hz), 4.85(t,1H,J=5.4 Hz), 5.02(d,1H,J=5.4 Hz), 5.08(d,1H,J=5.4 Hz), 7.08(d,2H,J=8.7 Hz), 7.2–7.4(m,2H), 7.61(dd,1H,$J_1$=0.8 Hz,$J_2$=7.1 Hz), 7.86(d,2H,J=8.7 Hz), 7.94(s,1H), 8.25(dd,1H,$J_1$=0.8 Hz,$J_2$=7.1 Hz).

MS: M+: 385, m/z: 324, 311, 250, 144, 121.

3-(o-hydroxybenzoyl)-N-(2,3-dihydroxypropyl)indole (compound 19) (Yield: 18%).

m.p.: (oily substance),

IR(KBr): 3400, 1608, 1580, 1380, 740 cm$^{-1}$.

NMR(DMSO-$d_6$): δ=3.29(dd,1H,$J_1$=5.5 Hz,$J_2$=10.5 Hz), 3.41(dd,1H,$J_1$=5.5 Hz,$J_2$=10.5 Hz,3.7 -3.9(m,1H), 4.14(dd,1H,$J_1$=7.8 Hz,$J_2$=14.2 Hz), 4.42(dd,1H,$J_1$=3.2 Hz,$J_2$=14.2 Hz), 4.85(t,1H,J=5.5 Hz), 5.07(d,1H,J=5.7 Hz), 6.95(dt,1H,$J_1$=1.4 Hz,$J_2$=7.7 Hz), 6.99(dd,1H,$J_1$=1.4 Hz,$J_2$=7.7 Hz), 7.2–7.4(m,2H), 7.43(dt,1H,$J_1$=1.4 Hz,$J_2$=7.7 Hz), 7.61(dd,1H,$J_1$=1.4 Hz,$J_2$=7.7 Hz), 7.63(dd,1H,$J_1$=1.5 Hz,$J_2$=7.8 Hz), 7.93(s,1H), 8.20(dd,1H,$J_1$=1.5 Hz,$J_2$=7.0 Hz), 10.87(brs,1H).

MS: M+: 311, m/z: 250, 222, 191, 130.

3-[o-(2,3-dihydroxypropoxy)benzyl]-N-(2,3-dihydroxypropyl)indole (compound 20) (Yield: 46%).

m.p.: (oily substance).

IR(KBr): 3340, 2925, 1600, 1520, 1385 cm$^{-1}$.

NMR(DMSO-$d_6$): δ=3.1–3.3(m,4H), 3.6–3.7(m,1H), 3.7–3.8(m,1H), 3.93(ddd,1H,$J_1$=4.3 Hz,$J_2$=5.5 Hz,$J_3$=10.0 Hz), 4.00(ddd,1H,$J_1$=2.5 Hz,$J_2$=4.8 Hz,$J_3$=10.0 Hz), 4.07(dd,1H,$J_1$=8.0 Hz,$J_2$=14.2 Hz), 4.37(dd,1H,$J_1$=3.0 Hz,$J_2$=14.2 Hz), 4.54(t,1H,J=5.7 Hz), 4.80(d,1H,J=5.7 Hz), 4.83(t,1H,J=5.7 Hz), 5.07(d,1H,J=5.7 Hz), 7.05(dt,1H,$J_1$=1.4 Hz,$J_2$=7.2 Hz), 7.18(dd,1H,$J_1$=1.4 Hz,$J_2$=7.2 Hz), 7.2–7.3(m,2H), 7.33(dd,1H,$J_1$=1.4 Hz,$J_2$=7.2 Hz), 7.46(dt,1H,$J_1$=1.4 Hz,$J_2$=7.2 Hz), 7.59(dd,1H,$J_1$=1.2 Hz,$J_2$=7.0 Hz), 7.67(s,1H), 8.22(dd,1H,$J_1$=1.2 Hz,$J_2$=7.1 Hz).

MS: M+: 385, m/z: 354, 325, 264, 250, 191, 130.

EXAMPLE 9

5 g of 3-(p-methoxybenzoyl)indole were dissolved in 30 ml of dimethylformamide containing 1.3 g of sodium methoxide. 1.93 g of 2-chloroethanol was added to the solution followed by stirring at 110° C. for 1 hour. The solution was concentrated under reduced pressure and was extracted with 100 ml of chloroform and 50 ml of water. After evaporating the organic layer to dryness, the residue was recrystallized from ethanol to give 3-(p-methoxybenzoyl)-N-(2-hydroxyethyl)indole (compound 21). (Yield: 51%).

m.p.: 133°–135° C.,

IR(KBr): 3400, 2950, 2910, 1600, 1592, 1380 cm$^{-1}$.

NMR(DMSO-$d_6$): δ=3.75(dt,2H,$J_1$=5.4 Hz,$J_2$=5.4 Hz), 3.86(s,3H), 4.33(t,2H,J=5.4 Hz), 4.95(t,1H,J=5.4 Hz), 7.08(d,2H,J=8.7 Hz), 7.2–7.4(m,2H), 7.62(dd,1H,$J_1$=1.8 Hz,$J_2$=7.7 Hz), 7.81(d,2H,J=8.7 Hz), 7.97(s,1H), 8.25(dd,1H,$J_1$=1.8 Hz,$J_2$=7.7 Hz).

MS: M+: 295, m/z: 264, 188, 135.

In the same way, the following compound was obtained.

3-(o-methoxybenzoyl)-N-(2,3-dihydroxypropyl)indole (compound 22) (Yield: 74%).

m.p.: (oily substance),

IR(KBr): 3320, 2920, 1600, 1390, 758 cm$^{-1}$.

NMR(DMSO-$d_6$): δ=3.2–3.4(m, 2H), 3.7–3.8(m,1H), 3.72(s,3H), 4.06(dd,1H,$J_1$=7.7 Hz,$J_2$=14.3 Hz), 4.35(dd,1H,$J_1$=3.4 Hz,$J_2$=14.3 Hz), 4.81(t,1H,J=5.8 Hz), 5.02(d,1H,J=5.4 Hz), 7.05(dt,1H,$J_1$=1.4 Hz,$J_2$=7.2 Hz), 7.16(dd,1H,$J_1$=1.4 Hz,$J_2$=7.2 Hz), 7.2–7.3(m,2H), 7.30(dd,1H,$J_1$=1.4 Hz,$J_2$=7.2 Hz), 7.47(dt,1H,$J_1$=1.4 Hz,$J_2$=7.2 Hz), 7.58(dd,1H,$J_1$=1.5 Hz,$J_2$=7.0 Hz), 7.61(s,1H), 8.17(dd,1H,$J_1$=1.5 Hz,$J_2$=7.0 Hz).

MS: M+: 325, m/z: 308, 264, 135, 77.

EXAMPLE 10

5 g of 3-(p-hydroxybenzoyl) indole were dissolved in 50 ml of dimethylformamide containing 2.28 g of sodium methoxide. 4.0 g of 3-chloropropanol was added to the solution followed by stirring at 110° C. in oil bath for 3 hours. After cooling, the solution was concentrated and extracted with 100 ml of ethyl acetate and 50 ml of water. The organic layer obtained was concentrated, and then the residue was purified by column chromatography on silica gel. Crude product was recrystallized from ethyl acetate to give 3-[p-(3-hydroxypropoxy)benzoyl]indole (compound 23) in the form of white needle crystals. (Yield: 30.5%).

m.p.: 184°–185° C.,

IR(KBr): 3460, 3440, 3180, 2860, 1602, 1258 cm$^{-1}$.

NMR(DMSO-$d_6$): δ=1.91(tt,2H,$J_1$=6.2 Hz,$J_2$=6.2 Hz), 3.59(dt,2H,$J_1$=6.2 Hz,$J_2$=6.2 Hz), 4.14(t,2H,J=6.2 Hz), 4.59(t,1H,J=6.2 Hz), 7.06(d,2H,J=8.7 Hz), 7.1–7.3(m,2H), 7.51(dd,1H,$J_1$=1.5 Hz,$J_2$=7.0 Hz), 7.79(d,2H,J=8.7 Hz), 7.94(s,1H), 8.21(dd,1H,$J_1$=1.5 Hz,$J_2$=7.0 Hz), 12.00(brs,1H).

MS: M+: 295, m/z: 236, 220, 144, 116, 89.

In the same way, the following compound was obtained.

3-[p-(3-hydroxypropoxy)benzoyl]-N-(3-hydroxypropyl)indole (compound 24) (Yield: 40.3%).

m.p.: 132°–133° C.,

IR(KBr): 3260, 2940, 1602, 1588, 1384 cm$^{-1}$.

NMR(DMSO-$d_6$): δ=1.8–2.0(m,4H), 3.38(dt,2H,$J_1$=6.2 Hz,$J_2$=6.2 Hz), 3.59(dt,2H,$J_1$=6.2 Hz,$J_2$=6.2 Hz), 4.15(t,2H,J=6.2 Hz), 4.35(t,2H,J=6.2 Hz), 4.59(t,1H,J=6.2 Hz), 4.66(t,1H,J=6.2 Hz), 7.07(d,2H,J=8.7 Hz), 7.2–7.4(m,2H), 7.62(dd,1H,$J_1$=1.5 Hz,$J_2$=7.0 Hz), 7.79(d,2H,J=8.7 Hz), 8.00(s,1H), 8.24(dd,1H,$J_1$=1.5 Hz,$J_2$=7.0 Hz).

MS: M+: 353, m/z: 323, 309, 295, 202, 179, 144, 121

The following description serves to illustrate pharmacological studies of the compounds of the present invention.

(1) Acute toxicity test 4000 mg/kg of the compound of the invention were orally administered to groups of 5 ddy-strain male mice which were fasted for 18 hours.

As a result, each compound of numbers of 1, 2, 3, 4, 5, 6, 7, 8 and 9 of the invention was tested and none of the mice were died.

(2) Inhibition of platelet-aggregation

Groups of 5 Wistar-strain male rats (weighing 250–300 g) were used for collection of blood from abdominal aorta in the presence of sodium citric acid under anesthesia with ether. The obtained material was centrifuged at 200×g for 8 minutes to give Platelet Rich Plasma (PRP) from the supernatant. Further centrifugation was carried out at 1500×g for 15 minutes to obtain Platelet Poor Plasma (PPP) from the supernatant.

Platelet-aggregation was measured by aggregometer. 5 μl of the solution of the examined compound was added to 450 μl of the above-mentioned PRP and incubated for 1 minute at 37° C., after that a coagulant was added thereto. Collagen was used as the coagulant (final concentration was 4 μg/ml). Test compound was dissolved in DMSO (dimethylsulfoxide). An example of the results is shown in Table 1.

TABLE 1

| Test Compound | Concentration (μM) | Platelet Aggregation (%) | Inhibition rate (%) |
|---|---|---|---|
| control | — | 58 ± 1 | — |
| compound 1 | 300 | 22 ± 5 | 62 |
| compound 2 | 300 | 7 ± 4 | 90 |
| compound 3 | 300 | 7 ± 3 | 90 |
| compound 4 | 300 | 8 ± 5 | 83 |
| compound 5 | 200 | 33 ± 1 | 43 |
| compound 6 | 300 | 9 ± 3 | 84 |
| compound 7 | 300 | 7 ± 1 | 88 |
| compound 9 | 300 | 8 ± 3 | 83 |
| Aspirin | 300 | 23 ± 4 | 60 |

In the same manner as indicated above using Wister strain male rats weighing 500–700 g, example of the results is shown in Table 2.

TABLE 2

| Test Compound | $IC_{50}$ (μM) |
|---|---|
| compound 1 | 30 |
| compound 2 | 29 |
| compound 3 | 27 |
| compound 4 | 23 |
| compound 5 | 29 |
| compound 6 | 18 |
| compound 7 | 21 |
| compound 8 | 23 |
| compound 16 | 61 |
| compound 17 | 85 |
| compound 18 | 94 |
| compound 19 | 81 |
| compound 20 | 108 |
| compound 23 | 52 |
| compound 24 | 77 |
| Indomethacin | 27 |

As apparently shown by the above-mentioned results, the compounds of the present invention have an excellent inhibitory effect on collagen induced platelet-aggregation as well as low toxicity. Thus, the compounds of the invention are useful not only as preventive medicine or remedy for various diseases or symptoms caused by platelet-aggregation, such as thrombosis, cerebrovascular disorder, arteriosclerosis, ischemic heart disease (myocardial infarction or coronary arteriosclerosis), sinus thrombosis or thrombosis caused by hemodialysis, but also as inhibitors of platelet-aggregation on vascular walls during or after operation.

The compounds of the present invention may be administered in the free form or in the form of pharmaceutically acceptable salts, and may also be used alone or in combination with other pharmaceutically active components.

When formulated as pharmaceutical compositions, the compounds of the present invention may be combined with an appropriate pharmaceutically acceptable carrier or diluent in the usual way, and may be formulated into preparations for oral or parenteral administrations, such as tablets, capsules, powders, granules, suppositories and injections.

In case of oral preparations, the compounds of the invention may be used alone or combined with an appropriate additive to make tablets, powders, granules or capsules, e.g. with conventional diluent such as lactose, mannitol, corn starch or potato starch; with binder such as crystalline cellulose, cellulose derivatives, acacia, corn starch or gelatins; with disintegrator such as corn starch, potato starch or sodium carboxymethylcellulose; with lubricant such as talc or magnesium stearate; and if desired, with diluents, moistening agents, preservatives and flavoring agents.

As regards injectable forms, the compounds of the invention may be formulated by dissolving, suspending or emulsifying a prescribed amount thereof in aqueous or non-aqueous solvent such as distilled water for injection, physiological saline, Ringer's solution, vegetable oil, fixed oil, synthetic aliphatic acid glycerides, esters of higher aliphatic acids or propylene glycol; and if desired, with conventional additives such as solubilizers, isotonic agents, stabilizers, suspending agents, emulsifying agents, buffering agents and preservatives.

The desirable dose of the acylindole derivative of the present invention varies with the subject, route and period of administration. However, generally, it is recommended to administer orally 1 to 4,000 mg, preferably 10 to 2500 mg of the compounds daily to an adult. As for parental administration e.g. injections, doses in the order of one tenth to one third of the above oral dose are preferable as daily doses.

Some prescriptions of the pharmaceutical compositions are shown below as examples which contain the compounds of the present invention as active ingredients.

PRESCRIPTION EXAMPLE 1 (TABLET)

| component | Content of a tablet (mg) |
|---|---|
| an invented compound | 50 |
| lactose | 130 |
| corn starch | 60 |
| magnesium stearate | 10 |
| Total | 250 mg |

An invented compound, lactose and corn starch were mixed homogeneously, kneaded with water, and shaped into granules using a granulating machine. The granules were dried with warm air, mixed with magnesium stearate and shaped into tablets by a tablet machine.

PRESCRIPTION EXAMPLE 2 (CAPSULE)

| component | Content of a capsule (mg) |
|---|---|
| an invented compound | 200 |
| lactose | 120 |
| Total | 320 mg |

All of the components were mixed homogeneously and charged into hard capsules.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

We claim:

1. Acylindole derivatives of the formula (I):

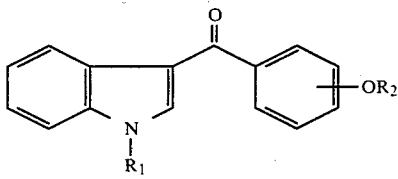

wherein $R_1$ is hydrogen, and $R_2$ is hydrogen, an alkyl group having 1 to 5 carbon atoms, an alkyl group having 1 to 5 carbon atoms containing one or more hydroxy groups, or a group of the formula

in which $R_3$ is an alkyl group having 1 to 5 carbon atoms, and wherein —$OR_2$ is substituted at the ortho or para position, and pharmaceutically acceptable salts thereof.

2. The acylindole derivatives according to claim 1, wherein $R_2$ is hydrogen or an alkyl group having 1 to 5 carbon atoms.

3. The acylindole derivative according to claim 2 which is 3-(p-hydroxybenzoyl)indole, 3-(o-hydroxybenzoyl)indole, 3-(p-methoxybenzoyl)indole, 3-(o-methoxybenzoyl)indole, 3-(p-ethoxybenzoyl)indole, or 3-(p-isopropoxybenzoyl)indole.

4. The acylindole derivatives according to claim 1 wherein $R_2$ is an alkyl group having 1 to 5 carbon atoms containing one or more hydroxy groups.

5. The acylindole derivative according to claim 4 which is 3-[p-(2-hydroxyethoxy)benzoyl]indole, 3-[p-(2,3-dihydroxypropoxy)benzoyl]indole, or 3-[p-(3-hydroxypropoxy)benzoyl]indole.

6. A platelet-aggregation inhibiting agent which comprises a pharmaceutically acceptable carrier and an effective amount of an acylindole derivative of the formula (I):

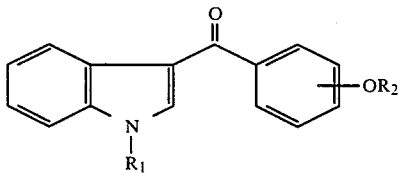

wherein $R_1$ is hydrogen, and $R_2$ is hydrogen, an alkyl group having 1 to 5 carbon atoms, an alkyl group having 1 to 5 carbon atoms containing one or more hydroxy groups, or a group of the formula

in which $R_3$ is an alkyl group having 1 to 5 carbon atoms, and wherein —$OR_2$ is substituted at the ortho or para position, or pharmaceutically acceptable salts thereof.

7. A platelet-aggregation inhibiting agent which comprises a pharmaceutically acceptable carrier and an effective amount of an acylindole derivative according to claim 2.

8. A platelet-aggregation inhibiting agent which comprises a pharmaceutically acceptable carrier and an effective amount of an acylindole derivative according to claim 3.

9. A platelet-aggregation inhibiting agent which comprises a pharmaceutically acceptable carrier and an effective amount of an acylindole derivative according to claim 4.

10. A platelet-aggregation inhibiting agent which comprises a pharmaceutically acceptable carrier and an effective amount of an acylindole derivative according to claim 5.

11. A method for treating mammals suffering from diseases caused by platelet-aggregation with at least one acylindole derivative of the formula (I):

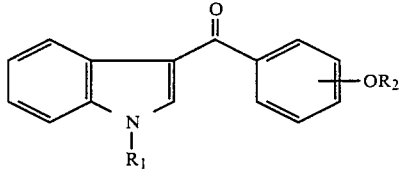

wherein $R_1$ is hydrogen, an alkyl group having 1 to 5 carbon atoms, or a group of the formula

and $R_2$ is hydrogen, an alkyl group having 1 to 5 carbon atoms, an alkyl group having 1 to 5 carbon atoms containing one or more hydroxy groups, or a group of the formula

in which $R_3$ is an alkyl group having 1 to 5 carbon atoms, and wherein —$OR_2$ is substituted at the ortho or para position, or pharmaceutically acceptable salts thereof.

12. A method for treating mammals suffering from diseases caused by platelet-aggregation with at least one acylindole derivative according to claim 2.

13. A method for treating mammals suffering from disease caused by platelet-aggregation with at least one acylindole derivative according to claim 3.

14. A method for treating mammals suffering from disease caused by platelet-aggregation with at least one acylindole derivative according to claim 4.

15. A method for treating mammals suffering from disease caused by platelet-aggregation with at least one acylindole derivative according to claim 5.

* * * * *